United States Patent [19]

Schmidt

[11] Patent Number: 5,139,788

[45] Date of Patent: Aug. 18, 1992

[54] NONCONTAMINATING ANTIMICROBIAL COMPOSITION

[75] Inventor: William Schmidt, Woodbury, Minn.

[73] Assignee: Ecolab Inc., St. Paul, Minn.

[21] Appl. No.: 569,237

[22] Filed: Aug. 17, 1990

Related U.S. Application Data

[63] Continuation of Ser. No. 422,778, Oct. 17, 1989, abandoned.

[51] Int. Cl.$^5$ .............................................. A61K 33/40
[52] U.S. Cl. ..................................... 424/616; 514/574
[58] Field of Search ................... 514/574; 424/332, 616

[56] References Cited

U.S. PATENT DOCUMENTS

| | | | |
|---|---|---|---|
| 349,852 | 9/1886 | Marchand | 426/332 |
| 1,772,975 | 8/1930 | Wieland | 514/574 |
| 3,297,456 | 1/1967 | Newell | 106/3 |
| 4,011,346 | 3/1977 | Ernst | 426/332 |
| 4,051,058 | 9/1977 | Bowing et al. | 252/186 |
| 4,051,059 | 9/1977 | Bowing et al. | 252/186 |
| 4,203,765 | 5/1980 | Claeys et al. | 430/252 |
| 4,534,945 | 8/1985 | Hopkins et al. | 423/273 |
| 4,557,935 | 12/1985 | af Ekenstam et al. | 424/130 |
| 4,900,721 | 2/1990 | Bansemir et al. | 514/35 |

FOREIGN PATENT DOCUMENTS

| | | |
|---|---|---|
| 1174976 | 9/1984 | Canada . |
| 250539 | 12/1986 | European Pat. Off. . |
| 59-164400 | 9/1984 | Japan . |
| 62-270509 | 11/1987 | Japan . |
| WO87/03779 | 7/1987 | PCT Int'l Appl. . |
| WO87/06470 | 11/1987 | PCT Int'l Appl. . |
| 1135643 | 12/1968 | United Kingdom . |
| 2076286A | 12/1981 | United Kingdom . |
| 2187097A | 10/1987 | United Kingdom . |
| 2189394A | 10/1987 | United Kingdom . |

OTHER PUBLICATIONS

Jones, Martin V. CA 108: 166345q 1988.
Alliger, Howand CA 102: 32300p 1985.
Kraus, Alfred CA 70: 60796u 1969.
Transactions of the Royal Society of Canada, Third Series, vol. XXI, Part II, Section III, dated May, 1927.
Mulder et al., "Research Note: Salmonella Decontamination of Broiler Carcasses (Chickens) with Lactic Acid, L-Cysteine, and Hydrogen Peroxide", *Poultry Science*, pp. 1555-1557 (1986).

*Primary Examiner*—Frederick E. Waddell
*Assistant Examiner*—Russell Travers
*Attorney, Agent, or Firm*—Merchant, Gould, Smith, Edell, Welter & Schmidt

[57] ABSTRACT

An antimicrobial surface sanitizing composition comprising a major portion of diluent and an active antimicrobial agent, said agent comprising an antimicrobial effective amount of an alpha-hydroxy substituted mono- or di-carboxylic acid, and an antimicrobial effective amount of hydrogen peroxide, wherein after contact with the intended surface said antimicrobial composition leaves a noncontaminating residue upon that surface.

20 Claims, No Drawings

NONCONTAMINATING ANTIMICROBIAL COMPOSITION

This is a continuation of application Ser. No. 07/422,778, filed Oct. 17, 1989, which was abandoned upon the filing hereof.

FIELD OF THE INVENTION

The invention generally relates to antimicro compositions which do not leave a contaminating residue upon application. More specifically, the invention relates to a carboxylic acid/peroxide antimicrobial composition which can provide high antimicrobial efficacy and prevent local environmental bacterial growth.

BACKGROUND OF THE INVENTION

The current state of the art provides a wide variety of antimicrobial agents which may be used for any number of purposes. While certain antimicrobial agents such as iodine based agents or quaternary surfactants have a high degree of antimicrobial efficacy, these agents can leave a residue which may be highly undesirable and in fact contaminating of many products or substances which may subsequently come in contact with the treated surface. Accordingly, the treated surface must often be cleansed of the antimicrobial agent by a post-treatment process prior to further use.

For example, hard surface cleaners in food processing environments, dairy compositions such as teat dips, food preparation dips such as those used for cleaning chicken carcasses as well as the human topical cleansers are all compositions which may require an effective antimicrobial agent which does not leave a contaminating residue on the surface of application. Contamination in the context refers to constituent or element resulting from the antimicrobial treatment which is undesirable on the cleaned surface or final product.

For example, present dairy processes generally use a premilking dipping of the dairy cow's udder to reduce environmental mastitis infections. While the practice of premilking dipping produces benefits in the reduction of infections, this process brings about additional, time consuming steps. Normally the process of premilking dipping requires that the cow's udder be dipped in the teat dip, and then wiped down. If the udder is not dried, the teat dip may remain on the udder and, in turn, may form a residue. Once milking is initiated this residue may contaminate the milking machine, and even the finished milk product.

Such contaminants are largely undesirable as most premilking teat dips comprise antimicrobial elements such as iodine, chlorohexidene, chlorine, or quaternary cationic surfactants. Federal regulations prohibit the sale of milk containing chlorohexidene or quaternary surfactant additives at any detectable level. Thus contamination may be avoided only by carefully wiping the udder down once the premilking dip is completed, prior to the actual milking processes.

Presently disclosed antimicrobial compositions provide a variety of constituents and characteristics. For instance, Bowing et al, U.S. Pat. Nos. 4,051,058 and 4,051,054 disclose antimicrobial compositions generally containing oxidizing compounds including peracetic or perpropionic acid. The disclosure of af Edenstam et al, U.S. Pat. No. 4,557,935 includes a germicidal skin ointment also containing hydrogen peroxide. Ekman et al disclosed in European Patent Application No. 250,539 an antimicrobial teat dip generally comprising hydrogen peroxide along with beta crystals of monoglyceride lipids.

However, the present state of the art has not provided a peroxide-acid composition having a durable and high antimicrobial efficacy when safely used in a topical application on mammalian skin. Moreover, the present state of the art has failed to provide an antimicrobial composition for topical application to prevent environmental mastitis infections which will avoid problems with leaving contaminants and residues within the finished milk product.

SUMMARY OF THE INVENTION

The composition of the invention has a high antimicrobial efficacy which is useful in the prevention of local environmental infections. Specifically, the antimicrobial composition of the invention may be used in applications such as premilking sanitizing operations without resulting in any antimicrobial contaminating residue within the resulting milk product. Moreover, the composition may be used in any number of other applications which require the application of a noncontaminating antimicrobial composition.

Accordingly, the antimicrobial composition of this invention comprises a major portion of diluent and an active antimicrobial agent which includes a hydroxy substituted carboxylic acid and hydrogen peroxide. Optionally the composition of the present invention may also comprise stabilizing agents, skin conditioning agents, and pigments among any variety of other agents useful in this invention.

DETAILED DESCRIPTION OF THE PRESENT INVENTION

The present composition generally comprises a major portion of diluent and an active antimicrobial agent. The antimicrobial agent comprises a hydroxy substituted carboxylic acid and hydrogen peroxide. This antimicrobial agent may provide sanitizing antimicrobial efficacy. Sanitizing antimicrobial efficacy is defined as a 5 log reduction in the number of colony forming units per cc of the given test organism. Optionally the composition may also comprise any number of adjuvants.

Carboxylic Acid

Among other constituents, the present composition comprises a carboxylic acid. Generally, carboxylic acids have the formula R—COOH wherein the R may represent any number of different groups including aliphatic groups, alicyclic groups, aromatic groups, heterocyclic groups, all of which may be saturated or unsaturated as well as substituted or unsubstituted. Carboxylic acids also occur having one, two, three or more carboxyl groups.

Carboxylic acids have a tendency to acidify aqueous compositions in which they are present as the hydrogen atom of the carboxyl group is active and may appear as an ion. The carboxylic acid constituent within the present composition when combined with aqueous hydrogen peroxide generally functions as an antimicrobial agent as a result of the presence of the active hydrogen atom. Moreover, the carboxylic acid constituent within the present composition maintains the composition at an acidic pH.

Carboxylic acids which are generally useful are those having one or two carboxyl groups where the R group is a primary alkyl chain having a length of $C_3$ to $C_6$ and which are freely water soluble. The primary alkyl chain is that carbon chain of the molecule having the greatest length of carbon atoms and directly appending carboxyl functional groups. Especially useful are mono- and di-hydroxy substituted carboxylic acids including alpha-hydroxy substituted carboxylic acid.

Especially preferred is lactic acid, also known as 2-hydroxypropionic acid, which has a formula of $CH_3CHOHCOOH$ and is a naturally occurring organic acid. Lactic acid has a molecular weight of 90.08 and is soluble in water, alcohol, acetone, ether and glycerol.

Lactic acid occurs naturally and may be produced by fermentation. Alternatively, lactic acid may be synthesized. Lactic acid occurs as optical isomers in the levo and dextro forms. Both optical isomers of lactic acid occur in nature.

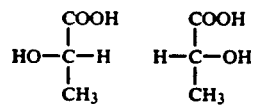

The concentration of lactic acid useful in the present invention generally ranges from about 0.25 weight percent to about 3.0 weight percent, preferably about 0.25 weight percent to about 2.5 weight percent, and most preferably from about 0.5 weight percent to about 2.0 weight percent. This concentration range of lactic acid is preferred for reasons of optimal acidity within the composition, as well as for the optimal antimicrobial efficacy which it brings to the topical antimicrobial system.

Generally, the preceding concentrations of lactic acid may be varied broadly while still providing a highly useful antimicrobial composition. For instance, reducing the concentration of lactic acid in comparison to any given concentration of hydrogen peroxide will essentially reduce the antimicrobial activity of the composition. Moreover, reducing the concentration of lactic acid may result in an increase in the pH of the composition and accordingly raise the potential for decreased antimicrobial activity.

In sharp contrast, increasing the concentration of lactic acid within the present composition may tend to increase the antimicrobial activity of the composition. Furthermore, increasing the concentration of lactic acid in the composition of the present invention will tend to decrease the pH of the composition. Preferably, the pH of the present composition will be 4 or less with a generally preferred pH in the composition being between 1.5 and 3.75, and a pH of about 2 and 3.5 being most preferred.

Hydrogen Peroxide

The antimicrobial composition of the present invention also comprises a hydrogen peroxide constituent. The hydrogen peroxide in combination with the lactic acid provides a surprising level of antimicrobial action against organisms including $E.$ $coli.$ Additionally, hydrogen peroxide provides an effervescent action at higher concentrations which irrigates the surface of application. Simply put, hydrogen peroxide provides a mechanical flushing action once applied which further cleans the surface of application.

Hydrogen peroxide, $(H_2O_2)$, has a molecular weight of 34.014 and is a weakly acidic, clear, colorless liquid. The four atoms are covalently bound in a nonpolar H—O—O—H structure. Generally, hydrogen peroxide has a melting point of $-0.41°$ C., a boiling point of $150.2°$ C., a density at $25°$ of 1.4425 grams per $cm^3$ and a viscosity of 1.245 centipose at $20°$ C.

While many oxidizing agents may be used, hydrogen peroxide is generally preferred for a number of reasons. First, when combined with a carboxylic acid at the intended concentrations, hydrogen peroxide contributes to a surprising antimicrobial efficacy many times that of either constituent used separately or other carboxylic acid/hydrogen peroxide mixtures. Moreover, after application of the $H_2O_2$/lactic acid germicidal agent the residue left merely comprises water and lactic acid. Deposition of these products on the surface of application such as a milking machine will not adversely affect the process or the finished milk product.

Generally, the concentration of hydrogen peroxide within the composition of the present invention ranges from about 0.1 weight percent to about 3 weight percent, preferably from about 0.25 weight percent to about 1.5 weight percent and most preferably from about 0.5 weight percent to about 1.0 weight percent. This concentration of hydrogen peroxide is most preferred as providing an optimal antimicrobial effect along with limiting the amount of irritation to the surface of application.

These concentrations of hydrogen peroxide may be increased or decreased while still remaining within the scope of the present invention. For example, increasing the concentration of hydrogen peroxide may increase the antimicrobial efficacy of the composition of the present invention. Furthermore increasing the $H_2O_2$ concentration may reduce the need to stabilize the hydrogen peroxide within the composition. Specifically, increasing the hydrogen peroxide concentration in the composition may provide a composition which has an extended shelf life. However, increasing the concentration of hydrogen peroxide past a certain level may raise the potential for irritating the surface of application.

In contrast, decreasing the concentration of hydrogen peroxide may decrease the antimicrobial efficacy of the composition and necessitate the use of an increased concentration of lactic acid. Moreover, decreasing the concentration of hydrogen peroxide may necessitate the use of some stabilizing agent to ensure that the composition of the present invention will remain stable over the intended time period. Decreasing the concentration of hydrogen peroxide may also be used to decrease the level of irritation of the antimicrobial composition of the present invention if the composition is applied topically.

Adjuvants

The antimicrobial composition of the present invention may also comprise any number of adjuvants. Specifically, the composition of the present invention may comprise stabilizing agents, wetting agents, skin conditioning agents as well as pigments or dyes among any number of constituents which may be added to the composition.

Stabilizing agents may be added to the composition of the present invention to stabilize the hydrogen peroxide and prevent the premature oxidation of this constituent within the composition of the present invention.

Chelating agents or sequestrants generally useful as stabilizing agents in the present invention include alkyl-diaminepolyacetic acid type chelating agents such as EDTA (ethylenediaminetetraacetate tetrasodium salt), acrylic and polyacrylic type stabilizing agents, phosphonic acid and phosphonate type chelating agents among others.

Preferable sequestrants include phosphonic acids and phosphonate salts including 1-hydroxyethyldene-1,1-diphosphonic acid ($CH_3C(PO_3H_2)_2OH$), amino[tri(methylenephosphonic acid)] ($N[CH_2PO_3H_2]_2$), ethylenediamine[tetra(methylene-phosphonic acid)], 2-phosphonobutane-1,2,4-tricarboxylic acid, as well as the alkali metal salts, ammonium salts, or alkaloyl amine salts such as mono, di, or triethanolamine salts.

Preferably, the stabilizing agent is used at a concentration ranging from 0.05 weight percent to about 0.5 weight percent of the composition, preferably from about 0.05 weight percent to about 0.3 weight percent of the composition, and most preferably, from about 0.1 weight percent to about 0.2 weight percent of the composition.

Also useful in the composition of the present invention are wetting agents. Wetting agents function to increase the penetrant activity of the antimicrobial composition of the present invention. Wetting agents which may be used in the composition of the present invention include any of those constituents known within the art to raise the surface activity of the composition of the present invention. For example, anionic surfactants such as carboxylate, sulfonate, and sulfate solubilizing groups having an alkyl chain ranging from about $C_5$ to about $C_{30}$ may all be used as wetting agents in the present composition.

For example, wetting agents useful in the present invention include carboxylate surfactants such as polyalkyloxycarboxylates and N-acylsarcosinates; useful sulfonates include alkylbenzene sulfonates, alpha olefin-sulfonates, and sulfonates with an ester, amide or ether linkages; useful sulfate wetting agents include sulfated alcohols, and sulfated alcohol ethoxylates, sulfated alkylphenols, sulfated acid, amides, and esters, sulfated natural oils and fats as well as agents such as the dioctyl ester of sodium sulfosuccinic acid.

Especially preferable are surfactants such as alkyl or alkyl aromatic sulfonates and sulfates such as alkylbenzene sulfate and sulfonate, and linear alkyl sulfates having a alkyl chain ranging in length from $C_6$ to $C_{20}$.

Generally, the composition of the wetting agent used within the present invention will range from about 0.1 weight percent to about 2.0 weight percent of the composition, preferably from about 0.1 weight percent to about 1.5 weight percent of the composition, and most preferably from about 0.25 weight percent to about 1.0 weight percent of the composition.

The composition of the present invention may also contain an emollient to lubricate, condition and generally reduce the irritation of the surface of application which may result from the antimicrobial agent. Generally, any water soluble or dispersible skin conditioning agent known to those of skill in this art may be used in the present invention. Preferred emollients to be used in the present invention include glycerine, propylene glycol, and sorbitol. These two compounds are preferred due to their ready commercial availability and their proven efficacy in reducing irritation.

Generally, the concentration of emollient within the present invention ranges from about 0.5 weight percent to about 10.0 weight percent of the composition, preferably from about 1.0 weight percent to about 8.0 weight percent of the composition, and most preferably from about 3.0 weight percent to about 6.0 weight percent of the composition.

A dye may also be used as an adjuvant within the composition of the present invention. Due to the diluted nature of these compositions, they may often be confused with a bucket of water and ingested. In order to avoid such an occurrence the antimicrobial composition of the present invention may be dyed so that it may clearly be identified.

The dye or pigment used in the composition of the present invention may be any organic or inorganic dye which is a chemically acceptable trace constituent on the surfaces to which it is to be applied including dairy cow udders and the resulting milk products. Generally, dyes which are useful in the composition of the present invention include F, D & C Yellow Nos. 5 and 6. Although any number of colorants may be used, these dyes are preferred due to their relative acceptability in various solid and liquid food systems.

Generally, the dyes or pigments used within the present invention may be present in a concentration ranging from about 0.001 wt-% to 0.01 wt-%, preferably from about 0.002 wt-% to 0.006 wt-%, and most preferably from about 0.002 wt-% to 0.004 wt-%.

The composition of the present invention may also contain viscosity enhancers or thickeners. In certain applications a low viscosity largely resembling the viscosity of a water system may be desirable. For instance, in premilking applications, the cow's udder is submersed in the dip and then the dip preferably drips or falls away from the skin surface. In such an application an enhanced viscosity may not be appropriate.

Once milking is completed, the cow's udder is generally recleansed with a post milking teat dip. The purpose of this teat dip is to prevent contamination or local microbial infection of the cow's udder while feeding in the field or barn between milkings. In such an instance, the teat dip is preferably formulated to have a higher viscosity so that a residual amount of the dip is retained upon on cow's udder.

Generally in this instance, the viscosity of the teat dip may be increased by any number of water soluble thickeners. Thickeners useful in the present invention are those which do not leave contaminating residue on the surface of application, i.e. constituents which are incompatible with food or other sensitive products in contact areas.

Generally, thickeners which may be used in the present invention include natural gums such as xanthan gum. Also useful in the present invention are cellulosic polymers, such as carboxy methyl cellulose. Generally, the concentration of thickener use in the present invention will be dictated by the desired viscosity within the final composition. However, as a general guideline, viscosity of thickener within the present composition ranges from about 0.1 wt-% to about 1.5 wt-%, preferably from about 0.1 wt-% to about 1.0 wt-%, and most preferably from about 0.1 wt-% to about 0.5 wt-%.

The present composition may also contain any other number of constituents such as fragrances, among other constituents which are well known to those skilled in the art and which may facilitate the activity of the present invention.

| Constituent | Concentration (wt-%) | | |
| --- | --- | --- | --- |
| | Useful | Working | Preferred |
| Carboxylic Acid | 0.25-3 | 0.25-2.5 | 0.5-2 |

-continued

| Constituent | Concentration (wt-%) | | |
|---|---|---|---|
| | Useful | Working | Preferred |
| Hydrogen Peroxide | 0.1-3 | 0.25-1.5 | 0.5-1 |
| Stabilizing Agent | — | 0-0.5 | 0.1-0.2 |
| Wetting Agent | — | 0.1-1.5 | 0.25-1 |
| Skin Conditioning Agent | — | 0.5-8 | 3-6 |
| Dye | — | 0.001-0.01 | 0.002-0.004 |
| Thickener | — | 0.1-2 | 0.1-0.5 |
| Diluent | q.s. | q.s. | q.s. |

USE OF THE PRESENT INVENTION

The composition of the present invention may be applied on the intended surface without the formation of any antimicrobial contaminating residue upon that surface. Application of the composition of the present invention provides a high antimicrobial efficacy which once applied leaves a residue which is noncontaminating. The residue resulting from the antimicrobial action of the present invention includes lactic acid, a carboxylic acid naturally found within the environment, and water, the natural by-product of hydrogen peroxide oxidation.

The composition of the present invention may be used in many environments where the provision of a noncontaminating high efficacy antimicrobial composition is desired. For example, the composition of the present invention may be used as a premilking or post-milking teat dip for dairy cows. Use of the present composition as a premilking teat dip avoids the necessity of drying in order to prevent the active antimicrobial agent potentially from contaminating the milking machine and, in turn, the milk product. Also, the provision for a teat dip having a water-like viscosity allows for the maximum amount of drainage from the udder surface.

When used as a postmilking teat dip, the composition of the present invention might be altered to have a higher viscosity. However, the lactic acid-hydrogen peroxide antimicrobial agent provides reaction products, (lactic acid and water) which will not contaminate the milk product.

The composition of the present invention may also be used in any variety of other environments where a post-processing wash or drying is not preferable or desired. For instance, the composition of the present invention may be used as a topical hand wash. Alternatively, given the high efficacy of the present composition against E. coli type organisms, the present composition may be used in a diaper wipe where the composition is contained in an absorbant synthetic or natural substrate. Moreover, the composition of the present invention may be used in food preparation environments on hard porous or nonporous surfaces. In these instances, it an antimicrobial agent which will not contaminate food products is preferred. For instance, certain surfaces within food preparation environments are porous and in fact will absorb any active antimicrobial. Consequently, a post disinfecting washing or drying may not always be effective in removing the antimicrobial from the food preparation surface.

In contrast, by using the composition of the present invention to clean the food preparation surfaces post treatment drying or washing is unnecessary. The present invention also avoids the potential for recontaminating the surface of application by such post-treatment processing.

Another use for the composition of the present invention is in the gutting and cleaning of animal food carcasses. In this instance, the present invention may be used as a carcass dip without concern that the composition will leave residual contaminants in the carcasses which may be undesirable.

WORKING EXAMPLES

An initial experiment was run using samples comprising solely lactic acid and hydrogen peroxide to determine the efficacy of each of these compositions against microbial organisms. In each instance a comparative example was used in accordance with AOAC sanitizing testing procedures. The initial control concentration of E. coli was $6.2 \times 10^7$ cfu/ml and the initial control concentration of S. aureus was $4.6 \times 10^7$ cfu/ml. In each instance the efficacy of the compositions was measured after a two minute contact time. The results are provided below

| Comparative Example | Composition | Log Reduction (CFU/ml) | |
|---|---|---|---|
| | | S. aureus | E. coli |
| A | 1% lactic acid (88% w/v) | 1.59 (trial 1) | 1.59 |
| | | 1.84 (trial 2) | 0.90 |
| B | 1% $H_2O_2$ (35% w/v) | 0.19 | 0.17 |
| C | 3% $H_2O_2$ (35% w/v) | 0.19 | 0.22 |

None of the Comparative examples provided a 2 log reduction of the selected organisms.

Working examples 1-9 representing the composition of the present invention were then formulated using an aqueous diluent, lactic acid, hydrogen peroxide, a hydrogen peroxide stabilizer 1-hydroxyethylidene-1,1-diphosphonic acid, and a glycerine conditioning agent. The pH of Working Examples 4, 5, and 6 was adjusted to 3.0 using a 50% weight volume solution of sodium hydroxide (NaOH).

Comparative examples 1-9 were formulated also using water, hydrogen peroxide, 1-hydroxyethylidene-1,1-diphosphonic acid, citric acid, and a glycerine conditioning agent. Here again, comparative examples 4, 5, and 6 were adjusted to a pH of 3.

TABLE 1

| EXAMPLE | COMPOSITION OF WORKING EXAMPLES (wt-%) | | | | | | | | |
|---|---|---|---|---|---|---|---|---|---|
| | 1 | 2 | 3 | 4 | 5 | 6 | 7 | 8 | 9 |
| Water | 91.00 | 90.00 | 89.00 | 91.00 | 90.00 | 89.00 | 92.40 | 91.40 | 90.40 |
| $H_2O_2$ (35% w/v) | 2.90 | 2.90 | 2.90 | 2.90 | 2.90 | 2.90 | 1.50 | 1.50 | 1.50 |
| 1-hydroxy-ethylidene-1,1-diphosphonic acid | 0.10 | 0.10 | 0.10 | 0.10 | 0.10 | 0.10 | 0.10 | 0.10 | 0.10 |
| Lactic Acid (88% w/v) | 1.00 | 2.00 | 3.00 | 1.00 | 2.00 | 3.00 | 1.00 | 2.00 | 3.00 |

TABLE 1-continued

| EXAMPLE | COMPOSITION OF WORKING EXAMPLES (wt-%) | | | | | | | | |
|---|---|---|---|---|---|---|---|---|---|
| | 1 | 2 | 3 | 4 | 5 | 6 | 7 | 8 | 9 |
| Glycerine | 5.00 | 5.00 | 5.00 | 5.00 | 5.00 | 5.00 | 5.00 | 5.00 | 5.00 |
| | 100 | 100 | 100 | 100 | 100 | 100 | 100 | 100 | 100 |
| pH | 2.27 | 2.21 | 2.18 | 2.31 | 2.24 | 2.19 | 2.38 | 2.26 | 2.2 |
| Adjusted to: | — | — | — | 3.00 | 3.01 | 3.00 | — | — | — |

TABLE 2

| EXAMPLE | COMPOSITION OF COMPARATIVE EXAMPLES (wt-%) | | | | | | | | |
|---|---|---|---|---|---|---|---|---|---|
| | 1 | 2 | 3 | 4 | 5 | 6 | 7 | 8 | 9 |
| Water | 91.00 | 90.00 | 89.00 | 91.00 | 90.00 | 89.00 | 92.40 | 91.40 | 90.40 |
| $H_2O_2$ (35% w/v) | 2.90 | 2.90 | 2.90 | 2.90 | 2.90 | 2.90 | 1.50 | 1.50 | 1.50 |
| 1-hydroxy-ethylidene-1,1-diphosphonic acid | 0.10 | 0.10 | 0.10 | 0.10 | 0.10 | 0.10 | 0.10 | 0.10 | 0.10 |
| Citric Acid | 1.00 | 2.00 | 3.00 | 1.00 | 2.00 | 3.00 | 1.00 | 2.00 | 3.00 |
| Glycerine | 5.00 | 5.00 | 5.00 | 5.00 | 5.00 | 5.00 | 5.00 | 5.00 | 5.00 |
| | 100 | 100 | 100 | 100 | 100 | 100 | 100 | 100 | 100 |
| pH | 2.29 | 2.21 | 2.14 | 2.25 | 2.15 | 2.09 | 2.27 | 2.21 | 2.14 |
| Adjusted to: | — | — | — | 3.00 | 3.00 | 3.00 | — | — | — |

ANTIMICROBIAL EFFICACY

Following the formulation of working examples 1-9 and comparative examples 1-9, AOAC sanitizing testing was performed in accordance with Germicidal and Sanitizer Test, Official Final Action, A. O. A. C. Methods of Analysis, Thirteenth Edition, 1980. The formulations were tested against $E.$ $coli$ with a 30 second exposure time the initial control concentration of $E.$ $coli$ was $6.3 \times 10^7$ CFU/ml. The results of the study are shown in Table 3.

TABLE 3

| WORKING EXAMPLE | Log Reduction $E.$ $coli$ (CFU/cc) | COMPARATIVE EXAMPLE | Log Reduction $E.$ $coli$ (CFU/cc) |
|---|---|---|---|
| 1 | >5.0 | 1 | 1.80 |
| 2 | >5.0 | 2 | 1.42 |
| 3 | >5.0 | 3 | 1.40 |
| 4 | >5.0 | 4 | 0.99 |
| 5 | >5.0 | 5 | 2.71 |
| 6 | >5.0 | 6 | >5.0 |
| 7 | >5.0 | 7 | 1.60 |
| 8 | >5.0 | 8 | 1.69 |
| 9 | >5.0 | 9 | 2.48 |

Five log reductions in colony forming units/cc were achieved for all samples with lactic acid regardless of concentration or peroxide concentration or pH adjustment. However, only one 5 log reduction was observed for the comparative example 6.

AOAC sanitizing testing was then performed on working examples 1-9 and comparative examples 6 using Germicidal and Sanitizer Test, Official Final Action, A. O. A. C. Methods of Analysis, Thirteenth Edition, 1980. In this instance the test organism was $S.$ $aureus$ having a control concentration of $1.6 \times 10^8$ CFU/ml and $E.$ $coli$ having a control concentration of $1.3 \times 10^8$ CFU/ml.

TABLE 4

| TEST SAMPLE | Log Reduction (CFU/cc) | |
|---|---|---|
| | $S.$ $aureus$ | $E.$ $coli$ |
| WORKING EXAMPLE 1 | >5.0 | — |
| WORKING EXAMPLE 2 | >5.0 | — |
| WORKING EXAMPLE 3 | >5.0 | — |
| WORKING EXAMPLE 4 | 2.60 | — |
| WORKING EXAMPLE 5 | >5.0 | >5.0 |
| WORKING EXAMPLE 6 | 2.76 | — |
| WORKING EXAMPLE 7 | >5.0 | — |
| WORKING EXAMPLE 8 | >5.0 | >5.0 |
| WORKING EXAMPLE 9 | >5.0 | — |
| COMPARATIVE EXAMPLE 6 | 1.55 | 2.75 |

Five log reductions were achieved for Working Examples 1-3, 5, and 7-9. Comparative Example 6 did not achieve a 5 log reduction of either $S.$ $aureus$ or $E.$ $coli$. These results seem to indicate that Comparative Example 6 may not be consistently effective as a high efficacy antimicrobial composition in view of the results in Table 3.

The above discussion, examples and data illustrated are a current understanding of the invention. However, since many variations of the invention can be made without departing from the spirit and scope of the invention. The invention relies wholly on the claims hereinafter appended.

I claim as my invention:

1. A antimicrobial sanitizer composition having a pH of 4 or less, said composition consisting essentially of: a diluent and an antimicrobial agent, said agent consisting essentially of:

(a) about 0.9 wt-% to 2.5 wt-% of lactic acid; and
    (b) about 0.25 wt-% to 3 wt-% hydrogen peroxide; wherein after contact with a surface, said composition leaves a noncontaminating residue.

2. The composition of claim 1 wherein the compositional pH ranges from about 1.5 to about 3.75.

3. The composition of claim 1 wherein the compositional pH ranges from about 2 to 3.5.

4. The composition of claim 1 wherein said agent further consists essentially of a stabilizing agent present in a concentration ranging from about 0.05 wt-% to about 0.5 wt-%.

5. The composition of claim 1 additionally comprising a wetting agent, said wetting agent present in a concentration ranging from about 0.1 wt-% to about 1.5 wt-%.

6. The composition of claim 1 additionally comprising a skin conditioning agent, said skin conditioning agent present in a concentration ranging from about 0.5 wt-% to about 8 wt-%.

7. The composition of claim 1 additionally comprising a dye, said dye present in a concentration ranging from about 0.001 wt-% to about 0.01 wt-%.

8. The composition of claim 1 additionally comprising a thickener, said thickener present in a concentration ranging from about 0.1 wt-% to about 1.5 wt-%.

9. A method of using a antimicrobial sanitizing composition having a pH of 4 or less, said composition consisting essentially of a diluent, and an antimicrobial agent, said agent consisting essentially of:
   (a) about 0.9 wt-% to 2.5 wt-% of lactic acid, and
   (b) about 0.25 wt-% to 3 wt-% hydrogen peroxide;
wherein after contact with a surface said composition leaves a noncontaminating residue, said method comprising the steps of applying said composition to the surface of application for a sufficient period to result in a sanitization of the intended surface.

10. The method of claim 9 wherein said antimicrobial composition is used as a predressing carcass dip.

11. The method of claim 9 wherein said antimicrobial composition is used as a hard surface cleaner.

12. The method of claim 9 wherein said antimicrobial composition is used as a human hand wash.

13. A mammalian test dip sanitizing composition having a pH of 4 or less, said composition consisting essentially of a diluent and an antimicrobial agent, said antimicrobial agent consisting essentially of:
   (a) about 0.9 wt-% to 2.5 wt-% lactic acid;
   (b) about 2.5 wt-% to 3 wt-% hydrogen peroxide; and
   (c) about 0.1 wt-% to 1 wt-% of a stabilizing agent;
wherein after contact with a surface said composition leaves a noncontaminating residue.

14. The composition of claim 13 wherein the compositional pH ranges from about 1.5 to about 3.75.

15. The composition of claim 13 wherein the compositional pH ranges from about 2 to 3.5.

16. The composition of claim 13 additionally comprising a wetting agent, said wetting agent present in a concentration ranging from about 0.25 wt-% to 1 wt-%.

17. The composition of claim 13 additionally comprising a skin conditioning agent, said skin conditioning agent present in a concentration ranging from about 3 wt-% to 6 wt-%.

18. The composition of claim 13 additionally comprising a dye, said dye present in a concentration ranging from about 0.002 wt-% to 0.004 wt-%.

19. The composition of claim 13 additionally comprising a thickener, said thickener present in a concentration ranging from about 0.01 wt-% to 1 wt-%.

20. A method of using a sanitizing mammalian teat dip composition having a pH of 4 or less, said composition consisting essentially of a diluent, and an antimicrobial agent, said agent comprising about 0.9 wt-% to 2.5 wt-% lactic acid, about 0.25 wt-% to 3 wt-% hydrogen peroxide, and about 0.1 wt-% to 1 wt-% of a stabilizing agent wherein upon application to the intended surface said composition leaves a noncontaminating residue, said method comprising the step of applying said composition to the surface of application for a sufficient time period to result in sanitization of the surface.

* * * * *

UNITED STATES PATENT AND TRADEMARK OFFICE
CERTIFICATE OF CORRECTION

PATENT NO. :   5,139,788

DATED      :   August 18, 1992

INVENTOR(S) :  William Schmidt

It is certified that error appears in the above-identified patent and that said Letters Patent is hereby corrected as shown below:

In Column 12, line 2, "2.5" should read --0.25--.

Signed and Sealed this

Twenty-first Day of September, 1993

Attest:

BRUCE LEHMAN

Attesting Officer    Commissioner of Patents and Trademarks